(12) United States Patent
Lee et al.

(10) Patent No.: US 11,957,665 B1
(45) Date of Patent: Apr. 16, 2024

(54) PHARMACEUTICAL COMPOSITION FOR PREVENTING OR TREATING ALOPECIA AREATA ACTING AS A FUNCTIONAL ANTAGONIST FOR S1PR1 AND S1PR4

(71) Applicant: NEXTGEN BIOSCIENCE CO., LTD., Seongnam-si (KR)

(72) Inventors: Bong Yong Lee, Seoul (KR); Yang Hae Park, Seoul (KR); Eun Jeong Kim, Seongnam-si (KR)

(73) Assignee: NEXTGEN BIOSCIENCE CO., LTD., Seongnam-si (KR)

( * ) Notice: Subject to any disclaimer, the term of this patent is extended or adjusted under 35 U.S.C. 154(b) by 0 days.

(21) Appl. No.: 18/474,522

(22) Filed: Sep. 26, 2023

Related U.S. Application Data

(63) Continuation of application No. PCT/KR2023/012725, filed on Aug. 28, 2023.

(60) Provisional application No. 63/418,071, filed on Oct. 21, 2022.

(51) Int. Cl.
*A61K 31/4192* (2006.01)
*A61P 17/14* (2006.01)

(52) U.S. Cl.
CPC .......... *A61K 31/4192* (2013.01); *A61P 17/14* (2018.01)

(58) Field of Classification Search
CPC ............................ A61K 31/4192; A61P 17/14
See application file for complete search history.

(56) References Cited

U.S. PATENT DOCUMENTS

| | | |
|---|---|---|
| 4,139,619 A | 2/1979 | Chidsey, III |
| 4,596,812 A | 6/1986 | Chidsey, III et al. |

FOREIGN PATENT DOCUMENTS

| | | |
|---|---|---|
| EP | 2 982 678 B1 | 9/2017 |
| EP | 3 603 636 A1 | 2/2020 |
| KR | 10-2010-0015857 A | 2/2010 |
| KR | 10-1127201 B1 | 4/2012 |
| KR | 10-2017-0087813 A | 7/2017 |
| KR | 10-2018-0110499 A | 10/2018 |
| KR | 10-2021-0105102 A | 8/2021 |
| KR | 10-2022-0124209 A | 9/2022 |
| WO | 2021/142030 A1 | 7/2021 |

OTHER PUBLICATIONS

Australian Office Action dated Nov. 22, 2023 in Australian Application No. 2023248144.
International Search Report dated Dec. 14, 2023 in International Application No. PCT/KR2023/012725.
Korean Office Action dated May 27, 2023 in Korean Application No. 10-2022-0145210.
Korean Office Action dated Jan. 3, 2023 in Korean Application No. 10-2022-0145210.
Piccini I., et al., "020 Sphingosine 1-phosphate receptor signalling promotes hair growth and inhibits perifollicular T-cell expansion and immune privilege collapse ex vivo", Journal of Investigative Dermatology, 2021, vol. 141, Issue 10, p. S152 (1 page total).
Hashimoto et al., "NLRP$_3$ inflammasome activation contributes to development of alopecia areata in C$_3$H/HeJ mice", Experimental dermatology, 2022, vol. 31, No. 2, pp. 133-142 (12 pages total).

*Primary Examiner* — Kamal A Saeed
(74) *Attorney, Agent, or Firm* — Sughrue Mion, PLLC

(57) ABSTRACT

The present invention relates to a pharmaceutical composition for preventing or treating alopecia areata acting as a functional antagonist for S1P receptor's subtypes S1PR1 and S1PR4, and more particularly, relates to a pharmaceutical composition containing as an active ingredient a sphingolipid compound acting as a functional antagonist for S1PR1 and S1PR4, does not cause cardiovascular side effects, and is effective in preventing or treating alopecia areata.

10 Claims, 6 Drawing Sheets

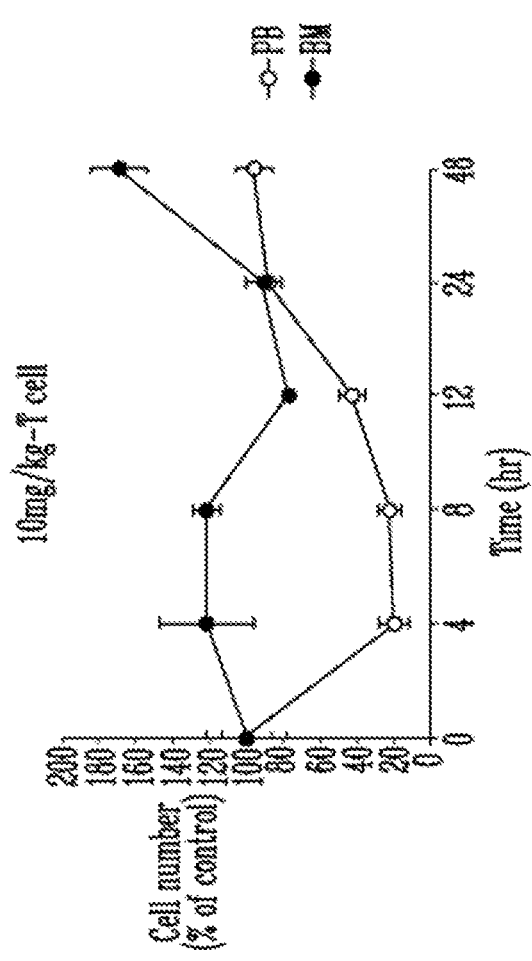
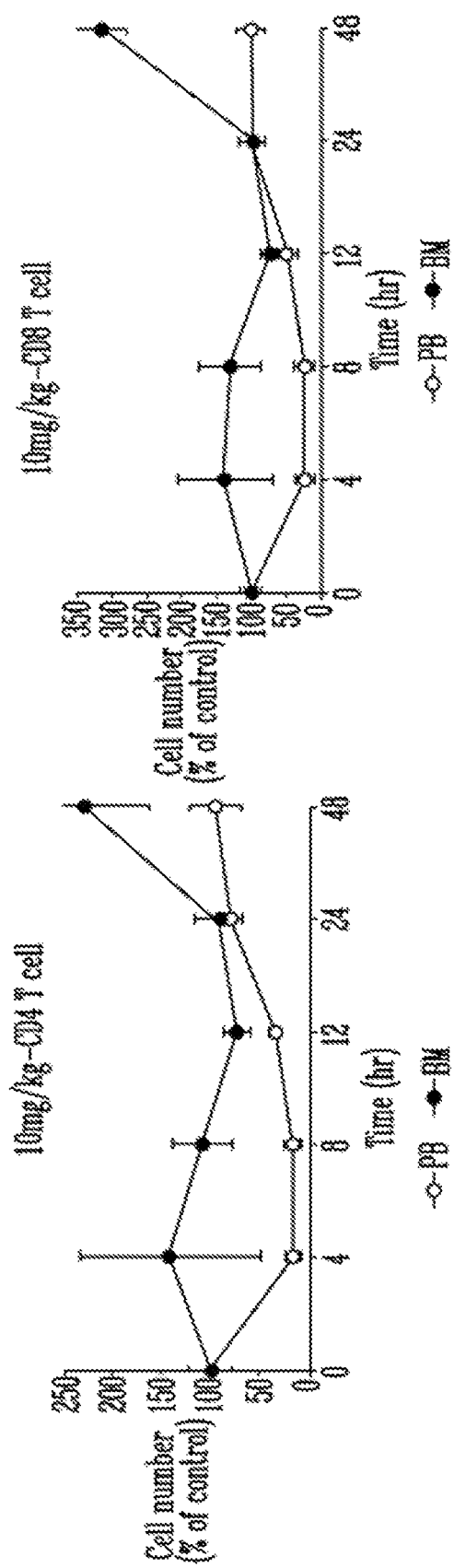
FIG. 2

AV±SD; $p^{**}<0.01$, $p^*<0.05$ vs NXC736 _ Mann-Whitney test $p^*<0.05$ _ Gehan-Breslow-Wilcoxon test

| Group / Concentration (μM) | | $I_{init}$ (pA) | $I_{drug}$ (pA) | $I_{rel}$ | Suppression rate (%) | Compensated suppression rate (%) | IC$_{50}$ (μM) | H |
|---|---|---|---|---|---|---|---|---|
| A<br>0 | Mean<br>S.D.<br>N | 1279<br>50<br>3 | 1238<br>37<br>3 | 0.9682<br>0.0399<br>3 | 3.18<br>3.99<br>3 | 0.00<br>4.12<br>3 | 12.94 | 1.527 |
| B<br>1 | Mean<br>S.D.<br>N | 894<br>254<br>3 | 783<br>234<br>3 | 0.8720<br>0.0190<br>3 | 12.80<br>1.90<br>3 | 9.94<br>1.96<br>3 | | |
| C<br>3 | Mean<br>S.D.<br>N | 1147<br>371<br>3 | 953<br>295<br>3 | 0.8328<br>0.0434<br>3 | 16.72<br>4.34<br>3 | 13.98<br>4.48<br>3 | | |
| D<br>10 | Mean<br>S.D.<br>N | 1250<br>1085<br>3 | 803<br>722<br>3 | 0.6291<br>0.1170<br>3 | 37.09<br>11.70<br>3 | 35.03<br>12.09<br>3** | | |
| E<br>30 | Mean<br>S.D.<br>N | 988<br>289<br>3 | 170<br>107<br>3 | 0.1683<br>0.0707<br>3 | 83.17<br>7.07<br>3 | 82.62<br>7.31<br>3** | | |
| F<br>0.1 | Mean<br>S.D.<br>N | 1427<br>608<br>5 | 101<br>48<br>5 | 0.0712<br>0.0160<br>5 | 92.88<br>1.60<br>5 | 92.64<br>1.66<br>5*** | | |

A: Negative control group (External bath solution), B-E: Test substance group (NXC736), F: Positive control group (E-4031)
$I_{init}$: Pre-treatment current
$I_{drug}$: Treatment current
$I_{rel}$: Relative current
S.D.: Standard deviation
N: Number of cells
IC$_{50}$: The half-maximal inhibitory concentration
H: Hill coefficient
**$p<0.01$: Significantly different from the negative control group (A) by Dunnett's t-test.
***$p<0.01$: Significantly different from the negative control group (A) by Student's t-test.

FIG. 6

PHARMACEUTICAL COMPOSITION FOR PREVENTING OR TREATING ALOPECIA AREATA ACTING AS A FUNCTIONAL ANTAGONIST FOR S1PR1 AND S1PR4

CROSS REFERENCE TO RELATED APPLICATIONS

This application is a Rule 53(b) Continuation of International Application No. PCT/KR2023/012725 filed Aug. 28, 2023, which claims priority from U.S. Provisional Patent Application No. 63/418,071 filed Oct. 21, 2022, the entire disclosures of which are incorporated herein by reference.

TECHNICAL FIELD

The present invention relates to a composition for preventing or treating alopecia areata acting as a functional antagonist for S1PR1 and S1PR4, and more particularly, the present invention relates to a pharmaceutical composition comprising a sphingolipid compound that acts as a functional antagonist for S1PR1 and S1PR4, does not cause cardiovascular side effects, and is effective in preventing or treating alopecia areata.

BACKGROUND

Alopecia is a symptom in which hair falls out abnormally in large amounts, and it is mainly caused by hair loss, but abnormal hair loss from beards, eyebrows, pubic hair, armpit hair, and other areas is also referred to as alopecia.

Hair is produced in hair follicles, which are located in the dermis layer above the subcutaneous fat below the epidermis layer. Hair follicles are found in all parts of the body except the lips, palms, and soles, and new hair is created from the hair matrix at the base of the hair follicle. Living cells in the hair matrix proliferate and are pushed upward, and when these cells quickly dry out and die, they are compressed into a dense, hard mass that makes up the hair shaft. The hair shaft, made of dead protein, is covered with a delicate layer (cuticle) of plate-like scales.

The hair growth cycle consists of three stages: anagen, when hair grows most actively, followed by in turn catagen, when hair deterioration begins, and telogen, when hair growth stops. At the end of the telogen, hair falls out, and new hair grows from the hair follicle, starting a new cycle again. The anagen of eyebrows and eyelashes lasts about 1 to 6 months, and the anagen of hair lasts about 2 to 6 years, and generally, about 50 to 100 hair strands on the scalp fall out every day at the end of the telogen.

Among alopecia, alopecia areata is a disease in which hair falls out in circular shapes, and it refers to a phenomenon in which in the beginning, circular hair loss occurs in one or two areas, but as it gets worse, circular hair loss occurs in several areas simultaneously or the hair loss areas become fused, and hair on the eyebrows or beard is also lost in addition to the hair on the scalp. Alopecia areata is an autoimmune disease in which the immune system changes, causing immune cells to attack hair follicles and cause inflammation, and is known to be caused by stress and genetic causes. Less than 10% of patients with alopecia areata may be accompanied by other autoimmune diseases such as atopic dermatitis, thyroid disease, and pernicious anemia, and it occurs in both men and women and at all ages, but is most common among children and young adults, with a prevalence of approximately 1-2% of the population.

The representative therapeutic agent for alopecia areata is steroid preparation. To date, steroid injections, steroid preparations, immunosuppressants, etc. have been used as therapeutic agents, and treatment with steroids initially shows some effectiveness, but long-term treatment can actually worsen symptoms or cause side effects such as scalp inflammation, scalp depression, hypertension, weight gain, heartburn, and gastritis, and has a tendency to relapse.

Currently, the most commonly used drugs for alopecia treatment include 2,4-diamino-6-piperidinopyrimidine-3-oxide (aka 'Minoxidil', see U.S. Pat. Nos. 4,139,619 and 4,596,812), which has been approved by the FDA, and finasteride, a specific inhibitor of type II 5α-reductase.

Minoxidil preparation is a drug that induces hair growth by increasing blood flow through a vasodilating effect and supplying nutrients to the hair roots, and is known to be particularly effective in relieving alopecia symptoms in the whorl area, and the medicine that uses this as an active ingredient is marketed under the brand name Rogaine (trade name of Pharmacia & Upjohn Company). Rogaine is known to reduce alopecia by up to 10% and promote hair growth in men suffering from male pattern alopecia, but has disadvantages that it must be applied externally directly to the scalp area, must be used regularly over a long period of time, and is not very effective against alopecia in areas other than the whorl area.

The medicine using finasteride as an active ingredient is marketed under the brand name Propecia (trade name of Merck & Co., Inc.), and it is a pill for oral administration and is known to suppress alopecia by preventing the conversion of testosterone to dihydrotestosterone (DHT) by inhibiting the function of type II 5α-reductase, but it also requires continuous and regular administration, and it has some problems in that for some patients, it has side effects such as decreased libido and erectile dysfunction, and it can only be used by adult men, and it is not effective for alopecia areata.

Recently, Olumiant (ingredient name: Baricitinib), an oral JAK inhibitor known to treat rheumatoid arthritis, received FDA approval in June 2022 as the third alopecia drug and the first systemic treatment for alopecia areata. In addition, Pfizer also announced efficacy data similar to Olumiant after completing phase 3 trials of PF-06651600 (ingredient name: Ritlecitinib), a type of JAK inhibitor, and it was recently approved by the FDA. However, research results have reported that JAK inhibitors increase the risk of heart attack, stroke, and cancer, and so there is a continued need for the development of safe medicines with excellent alopecia areata treatment efficacy and low toxicity and side effects.

Therefore, the inventors have made extensive efforts to develop medicines that have excellent efficacy for alopecia areata and have less toxic and side effects, and have confirmed that the compounds according to the present invention bind to S1PR1 and S1PR4 receptors specifically to act as functional antagonists, thereby preventing or treating alopecia areata, and have completed the present invention.

SUMMARY OF THE INVENTION

Technical Problem

The present invention is directed to providing a pharmaceutical composition comprising as an active ingredient a compound that has pharmacological activity for preventing or treating alopecia areata and does not cause cardiovascular side effects.

In another aspect, the present invention is directed to providing a method for preventing or treating alopecia areata comprising administering the composition or the active ingredient in the composition to a subject in need thereof.

In yet another aspect, the present invention is directed to providing the composition or the active ingredient in the composition for use in the prevention or treatment of alopecia areata.

In yet another aspect, the present invention is directed to providing use of the composition or the active ingredient in the composition in the manufacture of a medicament for preventing or treating alopecia areata.

Technical Solution

The present invention provides a pharmaceutical composition for preventing or treating alopecia areata, comprising a compound represented by the following Formula 1, an optical isomer thereof, or a pharmaceutically acceptable salt thereof as an active ingredient:

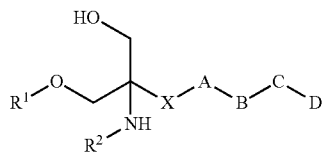

[Formula 1]

where,
R$^1$ is hydrogen;
R$^2$ is hydrogen or an acetyl group;
X is a single bond, C$_2$ is alkylene, or C$_2$ is alkenylene;
A is a 5-membered heteroarylene ring containing 3 N atoms;
B is C$_{2-11}$ straight- or branched-chain alkylene;
C is a single bond or phenylene; and
D is selected from the group consisting of hydrogen, phenyl and C$_{1-6}$ alkyl.

The R$^2$ may be hydrogen.
The X may be C$_2$ alkylene.
The B may be C$_{2-11}$ straight-chain alkylene.
The compound represented by Formula 1 may be any one compound selected from the group of compounds below:
(1) 2-amino-2-(2-(1-decyl-1H-1,2,3-triazol-4-yl)ethyl)propane-1,3-diol;
(2) 2-amino-2-(2-(1-octyl-1H-1,2,3-triazol-4-yl)ethyl)propane-1,3-diol;
(3) 2-amino-2-(2-(1-(4-hexylphenethyl)-1H-1,2,3-triazol-4-yl)ethyl)propane-1,3-diol;
(4) 2-amino-2-(1-dodecyl-1H-1,2,3-triazol-4-yl)propane-1,3-diol;
(5) (E)-2-amino-2-(1-decyl-1H-1,2,3-triazol-4-yl)vinyl-1,3-diol;
(6) 2-amino-2-(2-(1-(8-phenyloctyl)-1H-1,2,3-triazole-butyl-4-yl)ethyl)propane-1,3-diol;
(7) N-(2-(1-dodecyl-1H-1,2,3-triazol-4-yl)-1,3-dihydroxypropan-2-yl)acetamide;
(8) N-(4-(1-decyl-1H-1,2,3-triazol-4-yl)-1-hydroxy-2-(hydroxymethyl)butan-2-yl)acetamide; and
(9) N-(4-(1-(4-hexylphenethyl)-1H-1,2,3-triazol-4-yl)-1-hydroxy-2-(hydroxymethyl)butan-2-yl)acetamide.

The compound represented by Formula 1 may be a compound represented by Formula 2 below (hereinafter referred to as 'NXC736'):

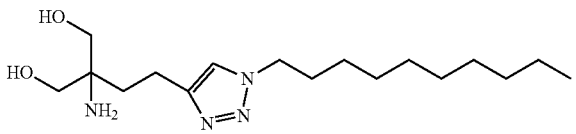

[Formula 2]

The pharmaceutical composition according to the present invention may be a preparation for oral administration or a preparation for parenteral administration.

The pharmaceutical composition according to the present invention may further comprise one or more other therapeutic agents suitable for the treatment of alopecia areata.

The pharmaceutical composition according to the present invention can act as a functional antagonist for S1PR1 and S1PR4.

The pharmaceutical composition according to the present invention can be expected to have the effect of not causing cardiovascular side effects.

The present invention provides a composition comprising a compound represented by Formula 1, an optical isomer thereof, or a salt thereof.

The present invention also provides a method for preventing or treating alopecia areata, comprising administering the composition or the active ingredient in the composition to a subject in need thereof.

The present invention also provides the composition or the active ingredient in the composition for use in the prevention or treatment of alopecia areata.

The present invention also provides use of the composition or the active ingredient in the composition in the manufacture of a medicament for preventing or treating alopecia areata.

Advantageous Effects

The pharmaceutical composition according to the present invention acts as a functional antagonist for S1PR1 and S1PR4 and has an effect in preventing or treating alopecia areata.

In particular, the pharmaceutical composition according to the present invention acts as a functional antagonist for S1PR1 and S1PR4 among subtypes of S1P receptors (S1P1, S1P2, S1P3, S1P4 and S1P5), thereby having an effect of preventing or treating alopecia areata and also having an effect of not causing cardiovascular side effects.

BRIEF DESCRIPTION OF THE DRAWINGS

FIG. 2 is a graph showing changes in the number of total T cells and T cell subtypes in rats after oral administration of NXC736 (10 mg/kg/day).

FIG. 6 is a table evaluating the effect of NXC736 (1, 3, 10, 30 μM) on HEK293 cells overexpressing the hERG gene.

DETAILED DESCRIPTION OF THE EMBODIMENTS

Figure 1:
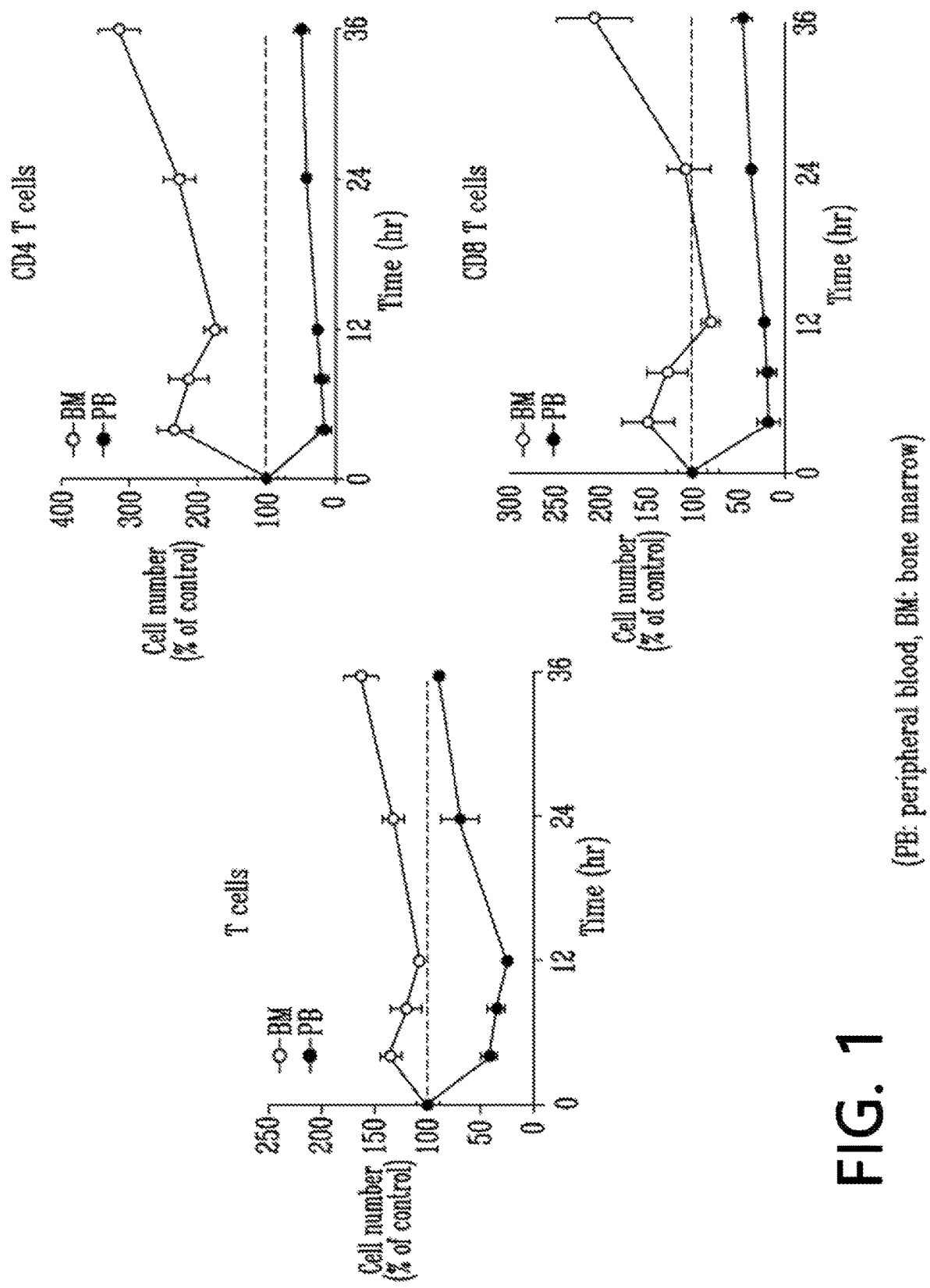
FIG. 1 is a graph showing changes in the number of total T cells and T cell subtypes in mice after oral administration of NXC736 (3 mg/kg/day).

The descriptions disclosed in this specification or application are merely illustrative for the purpose of explaining embodiments according to the technical idea of the present invention, and embodiments according to the technical idea of the present invention may be implemented in various forms other than the embodiments disclosed in this specification or application, and the technical idea of the present invention is not to be construed as being limited to the embodiments described in this specification or application.

The term "prevention" in the present invention refers to all actions that suppress or delay the onset of a target disease by administering an active ingredient to an individual.

The term "treatment" in the present invention refers to all actions that allow the symptoms of the target disease to be improved or beneficial by administering an active ingredient to an individual.

Hereinafter, the present invention will be described in detail.

The pharmaceutical composition for preventing or treating alopecia areata according to the present invention comprises a compound represented by the following formula 1, an optical isomer thereof, or a pharmaceutically acceptable salt thereof as an active ingredient.

[Formula 1]

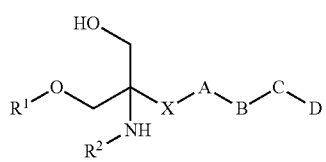

where,
R$^1$ is hydrogen;
R$^2$ is hydrogen or an acetyl group;
X is a single bond, C$_2$ is alkylene, or C$_2$ is alkenylene;
A is a 5-membered heteroarylene ring containing 3 N atoms;
B is C$_{2-11}$ straight- or branched-chain alkylene;
C is a single bond or phenylene; and
D is selected from the group consisting of hydrogen, phenyl and C$_{1-6}$ alkyl.
The R$^2$ may be hydrogen.
The X may be C$_2$ alkylene.
The B may be C$_{2-11}$ straight-chain alkylene.
In addition, the compound represented by Formula 1 may be any one compound selected from the group of compounds below:
(1) 2-amino-2-(2-(1-decyl-1H-1,2,3-triazol-4-yl)ethyl)propane-1,3-diol;
(2) 2-amino-2-(2-(1-octyl-1H-1,2,3-triazol-4-yl)ethyl)propane-1,3-diol;
(3) 2-amino-2-(2-(1-(4-hexylphenethyl)-1H-1,2,3-triazol-4-yl)ethyl)propane-1,3-diol;
(4) 2-amino-2-(1-dodecyl-1H-1,2,3-triazol-4-yl)propane-1,3-diol;
(5) (E)-2-amino-2-(1-decyl-1H-1,2,3-triazol-4-yl)vinyl-1,3-diol;
(6) 2-amino-2-(2-(1-(8-phenyloctyl)-1H-1,2,3-triazolebutyl-4-yl)ethyl)propane-1,3-diol;
(7) N-(2-(1-dodecyl-1H-1,2,3-triazol-4-yl)-1,3-dihydroxypropan-2-yl)acetamide;
(8) N-(4-(1-decyl-1H-1,2,3-triazol-4-yl)-1-hydroxy-2-(hydroxymethyl)butan-2-yl)acetamide; and
(9) N-(4-(1-(4-hexylphenethyl)-1H-1,2,3-triazol-4-yl)-1-hydroxy-2-(hydroxymethyl)butan-2-yl)acetamide.

In addition, the compound represented by Formula 1 may be 2-amino-2-(2-(1-decyl-1H-1,2,3-triazol-4-yl)ethyl)propane-1,3-diol (aka, NXC736), which is a compound represented by Formula 2 below.

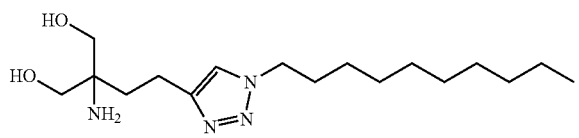 [SMILES: CCCCCCCCCCn1cc(CCC(N)(CO)CO)nn1]

The compound represented by Formula 1 can be used in the form of a pharmaceutically acceptable salt. In this case, the salt may be an acid addition salt formed from a pharmaceutically acceptable free acid.

In addition, the pharmaceutical composition according to the present invention not only may contain the compound represented by Formula 1 or a pharmaceutically acceptable salt thereof as an active ingredient, but also may contain as an active ingredient a substance selected from solvates, optical isomers, hydrates, etc. that can be prepared therefrom.

In the present invention, the compound represented by Formula 1, an optical isomer thereof, or a pharmaceutically acceptable salt thereof may be included in a pharmaceutically effective amount, for example, any amount within 0.1 to 99.9% by weight based on the total weight of the pharmaceutical composition.

A pharmaceutical composition for preventing or treating alopecia areata containing a compound represented by Formula 1, an optical isomer thereof, or a pharmaceutically acceptable salt thereof as an active ingredient can be changed into a preparation for oral administration and other type of preparation within the range of showing pharmacological activity.

Preparations for oral administration may be in the form of troches, lozenges, tablets, aqueous suspensions, oily suspensions, prepared powders, granules, emulsions, hard capsules, soft capsules, syrups, or elixirs, but are not limited to thereto.

In addition, in order to formulate the pharmaceutical composition according to the present invention into a preparation for oral administration, binding agents such as lactose, saccharose, sorbitol, mannitol, starch, amylopectin, cellulose or gelatin; excipients such as dicalcium phosphate; disintegrating agents such as maize starch or sweet potato starch; glydents such as magnesium stearate, calcium stearate, sodium stearyl fumarate or polyethylene glycol wax; sweetening agents; flavoring agents; syrups; and the like can be used. In addition, in the case of capsules, in addition to the above-mentioned substances, a liquid carrier such as fatty oil can be additionally used.

Pharmaceutical composition for preventing or treating alopecia areata containing a compound represented by Formula 1, an optical isomer thereof, or a pharmaceutically acceptable salt thereof as an active ingredient can be formulated and used in various suitable formulations for parenteral administration.

Preparations for parenteral administration include, but are not limited to, injections, suppositories, powders for respiratory inhalation, aerosols for sprays, ointments, powders for application, oils, and creams.

In addition, in order to formulate the pharmaceutical composition according to the present invention into a preparation for parenteral administration, sterilized aqueous solutions, non-aqueous solvents, suspensions, emulsions, freeze-dried preparations, topical preparations, etc. can be used. Specifically, non-aqueous solvents and suspensions may include propylene glycol, polyethylene glycol, vegetable oil such as olive oil, and injectable ester such as ethyl oleate, and the like.

When the pharmaceutical composition according to the present invention is formulated as an injection, the pharmaceutical composition may be mixed in water with a stabilizer or buffer to prepare a solution or suspension, which may be formulated for unit administration in ampoules or vials. In addition, when the pharmaceutical composition according to the present invention is formulated as an aerosol, a propellant, etc. may be mixed with additives to disperse the water-dispersed concentrate or wet powder. In addition, when the pharmaceutical composition according to the present invention is formulated into ointment, cream, etc., it may be formulated using animal oil, vegetable oil, wax, paraffin, starch, tragacanth, cellulose derivatives, polyethylene glycol, silicone, bentonite, silica, talc, zinc oxide, etc. as carriers.

The pharmaceutical composition according to the present invention may further include one or more other therapeutic agents suitable for the treatment of alopecia areata.

The one or more other therapeutic agents suitable for the treatment of alopecia areata may be administered together or separately. When administered separately, they may be administered simultaneously or sequentially in any order. The dosage and timing of administration of the compound of Formula 1 or a pharmaceutically acceptable salt thereof and other therapeutic agents may be selected to achieve the desired combination therapeutic effect.

The pharmaceutical composition according to the present invention may further include a pharmaceutically acceptable carrier. "Pharmaceutically acceptable" means that the compound does not irritate the organism upon administration and does not inhibit the biological activity and properties of the administered compound, as is commonly used in the pharmaceutical field.

The type of carrier is not particularly limited, and any carrier commonly used in the art can be used. Non-limiting examples of carriers include saline solution, sterile water, Ringer's solution, buffered saline solution, albumin injection solution, lactose, dextrose, sucrose, sorbitol, mannitol, xylitol, erythritol, maltitol, maltodextrin, glycerol, ethanol, etc. These may be used alone or in combination of two or more types.

In addition, if necessary, other pharmaceutically acceptable additives such as excipients, diluents, antioxidants, buffer solutions, or bacteriostatic agents may be added to the pharmaceutical composition according to the present invention. In addition, if necessary, fillers, extending agents, wetting agents, disintegrants, dispersants, surfactants, binders, or lubricants may be additionally added to the pharmaceutical composition according to the present invention.

The pharmacologically effective amount and dosage for the human body of the pharmaceutical composition according to the present invention may vary depending on the formulation method, administration method, administration time, and/or administration route, etc. of the pharmaceutical composition. The above dosage may vary depending on various factors including the type and degree of response to be achieved by administration of the pharmaceutical composition, the type of subject to be administered, age, weight, general health condition, symptoms or severity of the disease, gender, diet, excretion, and ingredients of other compositions, such as drugs, that are used simultaneously or concurrently to the subject, and similar factors well known in the medical field. In addition, the administration route and administration method of the pharmaceutical composition according to the present invention may be independent, and there is no particular limitation in the method. The pharmaceutical composition according to the present invention can be administered by any route and method of administration, as long as the active ingredient can reach the target area.

The pharmaceutical composition according to the present invention can be administered by oral or parenteral administration. For example, parenteral administration methods include intravenous administration, intraperitoneal administration, intramuscular administration, transdermal administration, or subcutaneous administration. In addition, the pharmaceutical composition according to the present invention may be applied or sprayed to the diseased area, or inhaled, but the method is not limited thereto. In addition, the pharmaceutical composition according to the present invention can be used for the treatment of alopecia areata in a subject in need thereof. In this case, the type of subject is not particularly limited, but may be a mammal, preferably a human.

In another aspect, the present invention provides a composition comprising a compound represented by Formula 1, an optical isomer thereof, or a salt thereof.

In yet another aspect, the present invention provides a method for preventing or treating alopecia areata including administering a compound represented by Formula 1, or an optical isomer thereof, or a pharmaceutically acceptable salt thereof, or a pharmaceutical composition containing the same to an individual in need thereof. The individual may be a human or a non-human animal.

In yet another aspect, the present invention provides a compound represented by Formula 1, an optical isomer thereof, a pharmaceutically acceptable salt thereof, or a pharmaceutical composition containing the same for use in the prevention or treatment of alopecia areata.

In yet another aspect, the present invention provides use of a compound represented by Formula 1, an optical isomer thereof, a pharmaceutically acceptable salt thereof, or a pharmaceutical composition containing the same in the manufacture of a medicament for preventing or treating alopecia areata.

The S1PR1 receptor is mainly present in lymphocytes and is mainly responsible for controlling the release of lymphocytes from immune cells. The S1PR4 receptor is also present in lymphocytes and not only acts on immune cell trafficking, but also acts on T cell regulation and thus is involved in inflammatory reactions. Therefore, the compound of the present invention not only acts as a functional antagonist of the S1PR1 receptor to inhibit the release of lymphocytes, but also acts on S1PR4 and exhibits an effective anti-inflammatory effect, thereby preventing or treating alopecia areata.

Specifically, the compound of the present invention act as a functional antagonist of S1PR1 and S1PR4 through a mechanism that specifically binds to the receptors and then enters the cell and eliminates them, thereby having the effect of preventing or treating alopecia areata.

In addition, the pharmaceutical composition according to the present invention acts as a functional antagonist for S1PR1 and S1PR4 and may not cause cardiovascular side effects.

The compound represented by Formula 1, an optical isomer thereof, or a pharmaceutically acceptable salt thereof acts as a functional antagonist for S1PR1 and S1PR4 and can prevent or treat alopecia areata without causing cardiovascular side effects.

Hereinafter, the present invention will be described in more detail through examples. These examples are only for illustrating the present invention, and it will be obvious to those skilled in the art that the scope of the present invention is not to be construed as limited by these examples.

Example—Preparation of a Compound Represented by Formula 1

The compound represented by Formula 1 of the present invention can be prepared through the method described in Korean Laid-Open Patent Publication No. 10-2017-0087813, and the method is the same as the Examples described below. However, the method for producing the compound represented by Formula 1 of the present invention is not limited thereto, and may be produced by a modified method within the range that can be modified by a person skilled in the art.

Example 1—Preparation of 2-amino-2-(2-(1-decyl-1H-1,2,3-triazol-4-yl)ethyl)propane-1,3-diol

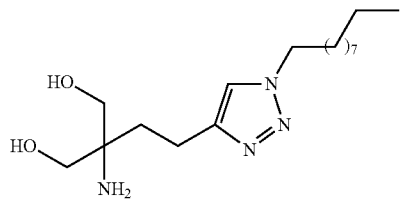

Step 1: Preparation of tert-butyl(2,2-dimethyl-5-((triisopropylsilyl)buta-1,3-diyn-1-yl)-1,3-dioxan-5-yl)carbamate

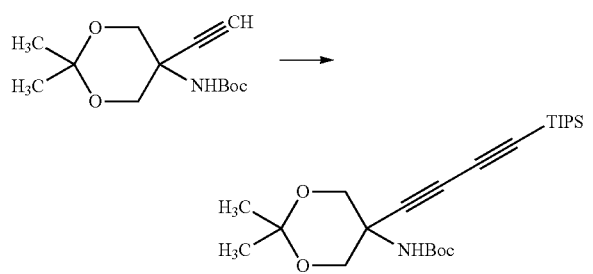

After tert-butyl 5-ethynyl-2,2-dimethyl-1,3-dioxan-5-yl carbamate (1.25 g, 4.89 mmol) dissolved in methanol (30 mL) was added to a solution of CuCl (10 mg, 0.10 mmol), $NH_2OH \cdot HCl$ (1.02 g, 14.67 mmol), and n-$BuNH_2$ (3.87 mL, 39.15 mmol) dissolved in methanol (50 mL) under $N_2$ gas conditions, 2-bromo-1-triisopropylsilyl acetylene (2.56 g, 9.78 mmol) dissolved in methanol (20 mL) was added dropwise thereto, the reaction mixture was well stirred at room temperature for 2 hours, and then the reaction was quenched with water and the resulting product was concentrated. After the concentrate was diluted with ethyl acetate and washed with brine, the organic layer was dried over $MgSO_4$, filtered in a vacuum state, and then concentrated. The resulting product was purified by flash column chromatography (hexane/EtOAc, 7:1) to prepare a target compound (1.85 g, 4.25 mmol, 87%) as a white solid.

Step 2: Preparation of tert-butyl(5-((1-decyl-1H-1,2,3-triazol-4-yl)ethynyl)-2,2-dimethyl-1,3-dioxan-5-yl)carbamate

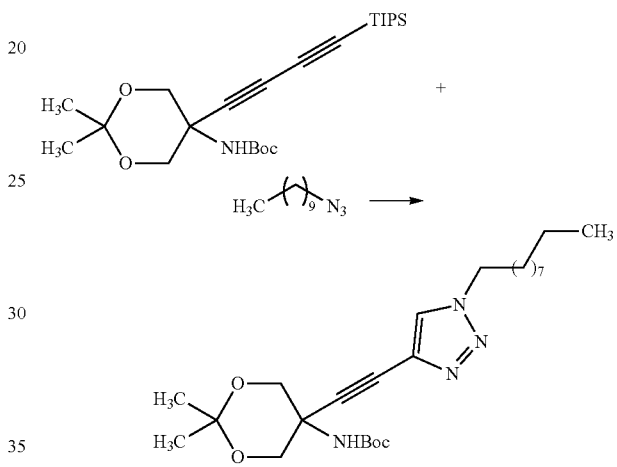

1-Azidodecane (339 mg, 1.86 mmol), CuI (114 mg, 0.60 mmol), N, N-diisopropylethylamine (DIPEA)(0.63 mL, 3.6 mmol) and AgF (182 mg, 1.44 mmol) were added to an anhydrous DMF (12 mL) solution in which the compound (334 mg, 1.20 mmol) prepared in Step 1 was dissolved. After the reaction mixture was well stirred at room temperature for 12 hours, the reaction was quenched with saturated $NH_4Cl$, and then the resulting product was extracted twice with ethyl acetate, and the organic layer extract was washed with saturated $NH_4Cl$ and brine. The product was dried over $MgSO_4$, and then concentrated under reduced pressure. The concentrate was purified by flash column chromatography (hexane/EtOAc, 6:1) to prepare a target compound (439 mg, 0.95 mmol, 79%) as a white solid.

Step 3: tert-butyl(5-(2-(1-decyl-1H-1,2,3-triazol-4-yl)ethyl)-2,2-dimethyl-1,3-dioxan-5-yl)carbamate

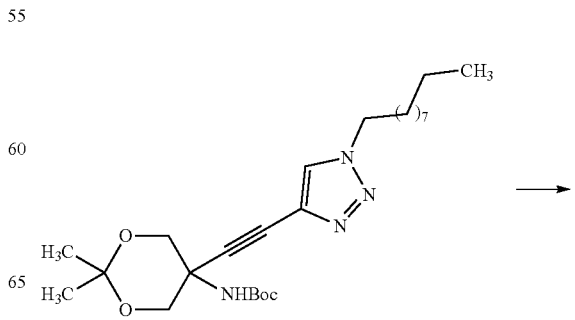

-continued

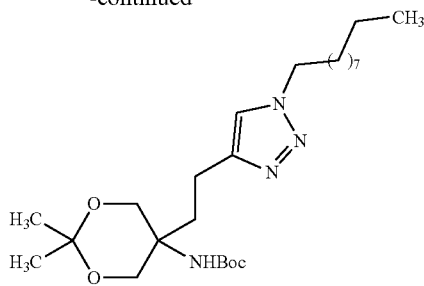

10% Pd/C (45 mg, 30 wt % of the compound prepared in Step 2) was added to a solution of the compound (149 mg, 0.32 mmol) prepared in Step 2 dissolved in methanol (30 mL). The flask was evacuated, and then filled with $H_2$ gas, the mixture was stirred at room temperature for 1 hour, filtered by Celite and concentrated, and then the precipitate was purified by flash column chromatography (hexane/EtOAc, 7:1 or 2:1) to prepare a target compound (110 mg, 0.24 mmol, 74%) as a colorless oil.

Step 4: Preparation of 2-amino-2-(2-(1-decyl-1H-1,2,3-triazol-4-yl)ethyl)propane-1,3-diol

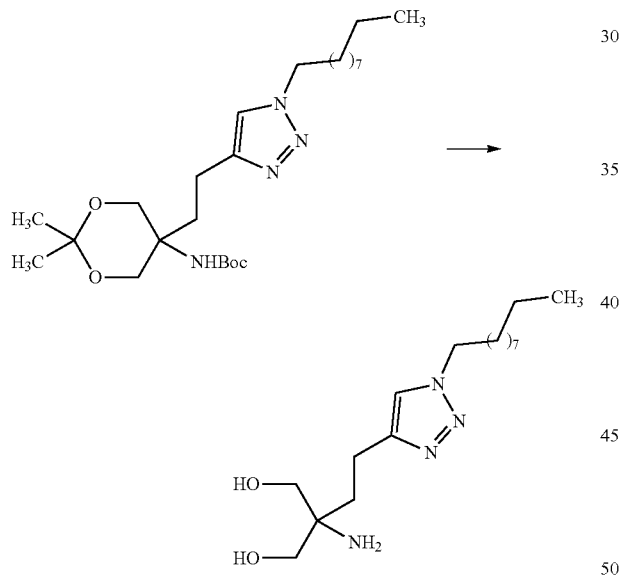

TFA (1.40 mL) was added to a $CH_2Cl_2$ (1.40 mL) solution in which the compound (65 mg, 0.14 mmol) prepared in Step 3 was dissolved at room temperature. The reactant was stirred for 12 hours, the solvent and the reagent were removed under reduced pressure, and then the concentrate was purified by flash column chromatography ($CH_2Cl_2$/MeOH/$NH_4OH$, 100:10:1) to prepare a target compound (36 mg, 0.11 mmol, 78%) as a while solid.

$^1$H NMR (400 MHz, $CDCl_3$) δ 0.86 (t, J=6.8 Hz, 3H), 1.23-1.29 (m, 14H), 1.85 (t, J=6.8 Hz, 2H), 1.92 (t, J=7.7 Hz, 2H), 2.47 (br s, 4H), 2.78 (t, J=7.8 Hz, 2H), 3.57 (dd, J=11.2, 26.9 Hz, 4H), 4.27 (t, J=7.3 Hz, 2H), 7.31 (s, 1H); $^{13}$C NMR (75 MHz, $CDCl_3$) δ 14.03, 19.21, 22.57, 26.50 (2C), 28.95 (2C), 29.03 (2C), 30.19, 31.70, 50.42, 60.05, 63.09 (2C), 121.34, 146.82; IR ($CHCl_3$) vmax; HRMS (FAB) calcd for $C_{17}H_{35}N_4O_2$ ($[M+H]^+$) 327.2760, found 327.2762.

Example 2—Preparation of 2-amino-2-(2-(1-octyl-1H-1,2,3-triazol-4-yl)ethyl)propane-1,3-diol

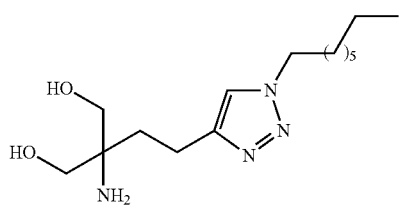

The target compound was prepared in the same manner as in the reaction process of Example 1, except that 1-azidooctane was used instead of 1-azidodecane.

$^1$H NMR (400 MHz, $CDCl_3$) δ 0.86 (t, J=6.8 Hz, 3H), 1.24-1.29 (m, 10H), 1.84-1.91 (m, 4H), 2.48 (br s, 4H), 2.77 (t, J=7.4 Hz, 2H), 3.54 (q, J=12.2 Hz, 4H), 4.28 (t, J=7.2 Hz, 2H), 7.28 (s, 1H).

Example 3—Preparation of 2-amino-2-(2-(1-(4-hexylphenethyl)-1H-1,2,3-triazol-4-yl)ethyl)propane-1,3-diol

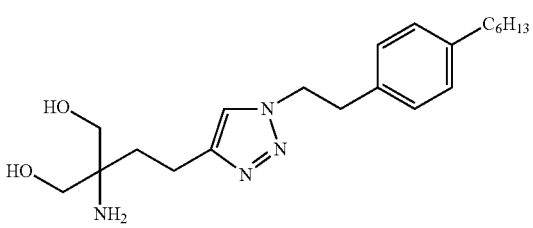

The target compound was prepared in the same manner as in the reaction process of Example 1, except that 1-(2-azidoethyl)-4-hexylbenzene was used instead of 1-azidodecane.

Example 4—Preparation of 2-amino-2-(1-dodecyl-1H-1,2,3-triazol-4-yl)propane-1,3-diol

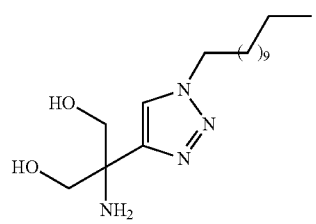

The target compound was prepared in the same manner as in Example 1, except that bromotriisopropylsilane was used instead of 2-bromo-1-triisopropylsilyl acetylene used in Step 1 of Example 1, and 1-azidododecane was used instead of 1-azidodecane in Step 2.

$^1$H NMR (300 MHz, MeOD) δ 0.89 (t, J=6.7 Hz, 3H), 1.28-1.32 (m, 18H), 1.90-1.92 (m, 2H), 3.89-3.98 (m, 4H), 4.41 (t, J=7.1 Hz, 2H), 8.07 (s, 1H).

Example 5—Preparation of (E)-2-amino-2-(1-decyl-1H-1,2,3-triazol-4-yl)vinyl-1,3-diol

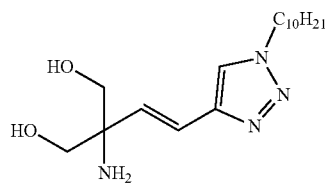

After the temperature of a THF (5 mL) solution, in which the compound prepared in Step 2 of Example 1 was dissolved, was lowered to −78° C., a THF solution (0.3 mmol), in which lithium aluminum hydride (LAH) was dissolved, was slowly added thereto. After the mixture was stirred 0° C. for 3 hours, the reaction was quenched with water, and the resulting product was extracted twice with CH$_2$Cl$_2$. The organic layer was washed with brine, dried over MgSO$_4$, and then concentrated under vacuum. The concentrate was purified by flash column chromatograph (CH$_2$Cl$_2$/MeOH, 20:1) to prepare a target compound as a white solid. Thereafter, the target compound was prepared in the same manner as in the reaction process of Step 4 of Example 1. (24 mg, 0.074 mmol, 74%)

Example 6—Preparation of 2-amino-2-(2-(1-(8-phenyloctyl)-1H-1,2,3-triazolbutyl-4-yl)ethyl)propane-1,3-diol

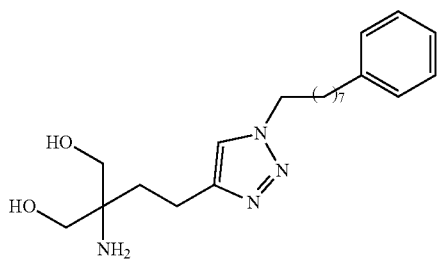

The target compound was prepared in the same manner as in Example 1, except that 8-azidooctylbenzene was used instead of 1-azidodecane used in Step 2 of Example 1.

Example 7—Preparation of N-(2-(1-dodecyl-1H-1,2,3-triazol-4-yl)-1,3-dihydrooxypropan-2-yl)acetamide

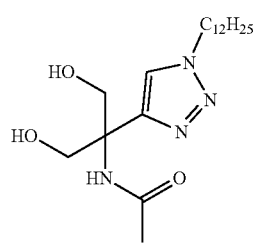

Acetic anhydride (0.2 mL), MeOH (1 mL), and an aqueous saturated NaHCO$_3$ solution (1 mL) were added to the compound (50 mg, 1 eq, 0.15 mmol) prepared in Example 4, the resulting mixture was stirred for 30 minutes, and then concentrated, the reaction was quenched with an aqueous ammonium chloride solution, and then the resulting product was extracted twice with CH$_2$Cl$_2$, dried over MgSO$_4$, and concentrated to prepare the target compound at a yield of 98% without a separate purification process (54 mg, 98%).

$^1$H NMR (300 MHz, MeOD) δ 0.89 (t, J=6.7 Hz, 3H), 1.28-1.32 (m, 18H), 1.86-1.96 (m, 2H), 2.00 (s, 3H), 4.02 (q, J=11.2 Hz, 4H), 4.35 (t, J=7.2 Hz, 2H), 7.84 (s, 1H).

Example 8—Preparation of N-(4-(1-decyl-1H-1,2,3-triazol-4-yl)-1-hydroxy-2-(hydroxymethyl)butan-2-yl)acetamide

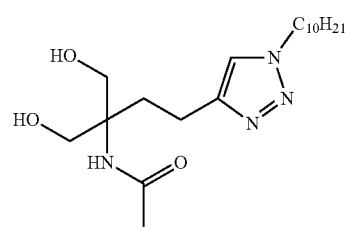

The target compound was prepared in a manner similar to the acetylation reaction performed in Example 7 using the compound prepared in Example 1 as a starting material.

$^1$H NMR (300 MHz, MeOD) δ 0.86 (t, J=6.8 Hz, 3H), 1.23-1.32 (m, 14H), 1.86-1.92 (m, 2H), 1.94 (s, 3H), 1.99-2.02 (m, 2H), 2.47 (m, 2H), 3.62 (dd, J=11.2, 26.9 Hz, 4H), 4.31 (t, J=7.3 Hz, 2H), 7.31 (s, 1H).

Example 9—Preparation of N-(4-(1-(4-hexylphenethyl)-1H-1,2,3-triazol-4-yl)-1-hydroxy-2-(hydroxymethyl)butan-2-yl)acetamide

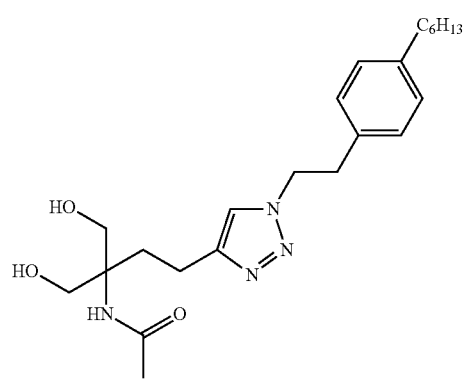

The target compound was prepared in a manner similar to the acetylation reaction performed in Example 7 using the compound prepared in Example 3 as a starting material.

Experimental Example 1: Confirmation of Inhibitory Effect of NXC736 on Mouse Immune Cells FTY720 (Fingolimod) is a therapeutic agent for multiple sclerosis that has a mechanism of action to reversibly capture a portion of lymphocytes in lymph nodes or bone marrow, isolating the lymphocytes into secondary lymphoid organs and inhibiting entry into the central nervous system, or to reduce the number of activated lymphocytes reaching the brain by reducing the number of lymphocytes circulating in the blood stream.

To determine whether NXC736, which acts on the S1P receptor, also has an effect on lymphocyte reduction, the effect of NXC736 on immune cells was evaluated. After oral administration of NXC736 once at 3 mg/kg/day to C57BL/6 mice (Daehan BioLink (DBL), 4 mice in the control group and 18 mice in the test group), the change in lymphocytes in peripheral blood (PB), bone marrow (BM) was measured by classifying into T cells (using anti-mouse CD3ε-PE/cyanine7 antibody), CD4 T cells (using anti-mouse CD4-FITC antibody), and CD8 T cells (using anti-mouse CD8a-PerCP antibody). Specifically, measurements were made using a flow cytometer (FC500, Beckman coulter) at 0, 4, 8, 12, 24, and 36 hours after administration of the test substance, the analysis was performed using FlowJo™ V10 (Flowjo, LLC), and the numbers of T cells, CD4 T cells, and CD8 T cells were expressed as % of control based on time 0.

Referring to FIG. 1, in the peripheral bloodstream (PB), it was confirmed that T cells, CD4 T cells, and CD8 T cells were reduced by 40.6 to 41.6%, 16.4 to 17.6%, and 5.9 to 9.3% after 4 hours, respectively, by administration of 3 mg/kg of NXC736. In the case of T cells, the decrease was maintained until 12 hours, and then gradually recovered, reaching 88.9% at 36 hours.

In bone marrow (BM), T cells were found to increase to 120 to 135% after 4 hours and to 118 to 131% after 24 hours by administration of 3 mg/kg of NXC736. This is judged to be a phenomenon that occurs when receptor internalization occurs by NXC736 and T cell release is suppressed.

After administration of 3 mg/kg of NXC736, it was confirmed that the number of T cells in the peripheral bloodstream (PB) steadily decreased for up to 12 hours, and the inhibitory effect was maintained to some extent until 24 hours before recovery. In conclusion, it was confirmed that administration of NXC736 resulted in a decrease in the number of lymphocytes circulating in the bloodstream and an immunosuppressive effect.

Experimental Example 2: Confirmation of Inhibitory Effect of NXC736 on Rat Immune Cells To evaluate the effect of NXC736 on rat immune cells, NXC736 was administered orally once at 10 mg/kg/day to SD rats (Daehan BioLink (DBL), 3 control groups, and 15 test groups), and then measurements were performed by classifying into T cells, CD4 T cells, and CD8 T cells in peripheral bloodstream (PB) and bone marrow (BM) using the same antibodies as in Experimental Example 1. Specifically, measurements were made using a flow cytometer (FC500, Beckman coulter) at 0, 4, 8, 12, 24, 36, and 48 hours after administration of the test substance, the analysis was performed using FlowJo™ V10 (Flowjo, LLC), and the numbers of T cells, CD4 T cells, and CD8 T cells were expressed as % of control based on time 0.

Referring to FIG. 2, it was confirmed that T cells were rapidly reduced in the peripheral bloodstream (PB) for up to 4 hours after administration of NXC736. It was confirmed that the immunosuppressive effect was maintained for up to 24 hours by administration of 10 mg/kg of NXC736. In bone marrow (BM), on the contrary, it was confirmed that there was no change in the number of lymphocytes or a tendency to increase.

Through this study, it was confirmed that NXC736 exhibits an immunosuppressive effect by reducing the number of lymphocytes in the peripheral bloodstream (PB) after oral administration. In addition, in bone marrow (BM), it was confirmed that there was no change in the number of lymphocytes or a tendency to increase. This effect is judged to be related to the mechanism by which NXC736 acts as a functional antagonist on the S1P receptor present in lymph nodes, bone marrow (BM), etc., thereby suppressing lymphocyte release.

Experimental Example 3: Confirmation of Efficacy in Suppressing Alopecia Areata Using C3H/HeJ Alopecia Areata Mouse Model The effectiveness of NXC736 for alopecia areata was evaluated using the alopecia areata mouse model C3H/HeJ (Jackson Lab, Saeron Bio). C3H/HeJ mice are experimental animals that naturally develop alopecia areata naturally when age of the week increased, and lymph node cells obtained from C3H/HeJ mice aged 20 weeks or older that naturally induced alopecia areata were proliferated, and alopecia areata was induced by injection into C3H/HeJ mice aged 10 to 16 weeks that did not develop alopecia areata. Conditions for the animal breeding room include a temperature of 23±3° C., relative humidity of 50±10%, and day and night maintained at 12-hour intervals, and experimental animals were raised in isolation breeding boxes (ThreeShine), and fed with food and drinking water for experimental animals ad libitum.

Mice were divided into two groups: the control group (sterilized distilled water administration group) and the NXC736 administration experimental group, five C3H/HeJ mice were randomly assigned per group, and from the time point lymph node cells were proliferated and injected into C3H/HeJ mice aged 10 to 16 weeks where no alopecia was induced, NXC736 was orally administered at 30 mg/kg for the NXC736 administration group and the same volume of sterilized distilled water was orally administered for the control group for 12 weeks once a day at the same time, respectively, and then the area of alopecia areata (AA) lesion area and disease free ratio were measured at intervals of 2 weeks.

The alopecia areata lesion area was measured using the Image J program (Version 1.44p) after taking a photograph.

Figure 3:
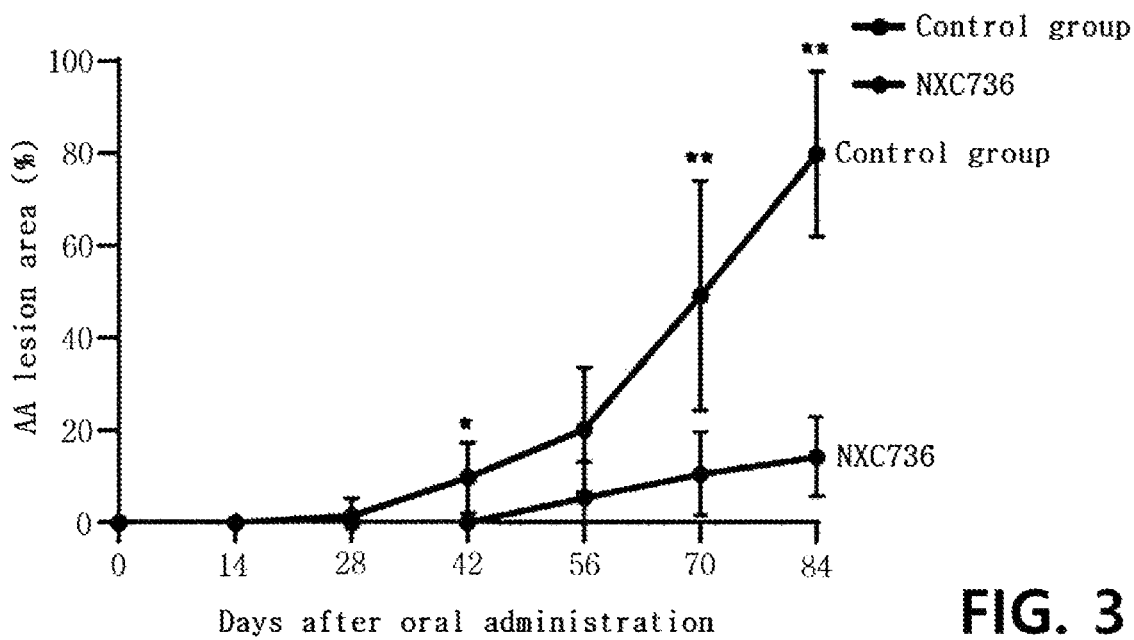
FIG. 3 shows the results of comparing the alopecia areata (AA) lesion area according to oral administration of control group and NXC736 (30 mg/kg/day) in alopecia areata mouse model C3H/HeJ.

Referring to FIG. 3, it was confirmed that alopecia areata (AA) lesion area was approximately 80% in the control group and approximately 10% in the NXC736 administration group, and the AA lesion area in the NXC736 administration group was significantly smaller than that in the control group.

The disease free ratio was defined as the proportion of mice administered the drug and not showing alopecia symptoms at a specified time point.

Figure 4:
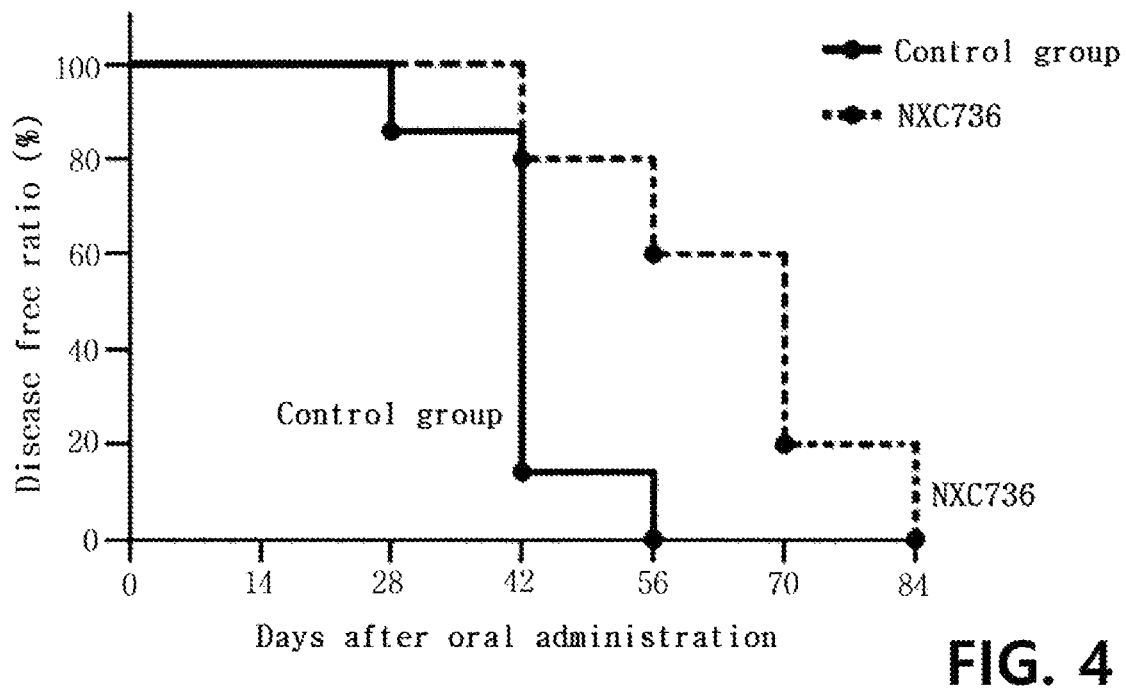
FIG. 4 shows the results of comparing disease free ratio according to oral administration of control group and NXC736 (30 mg/kg/day) in alopecia areata mouse model C3H/HeJ.

Referring to FIG. 4, as shown in the disease free ratio result graph, it was confirmed that it took 56 days for the control group to observe 100% alopecia areata, whereas the NXC736 administration group lasted up to 84 days, delaying the progression of alopecia areata upon NXC736 administration.

Figure 5:
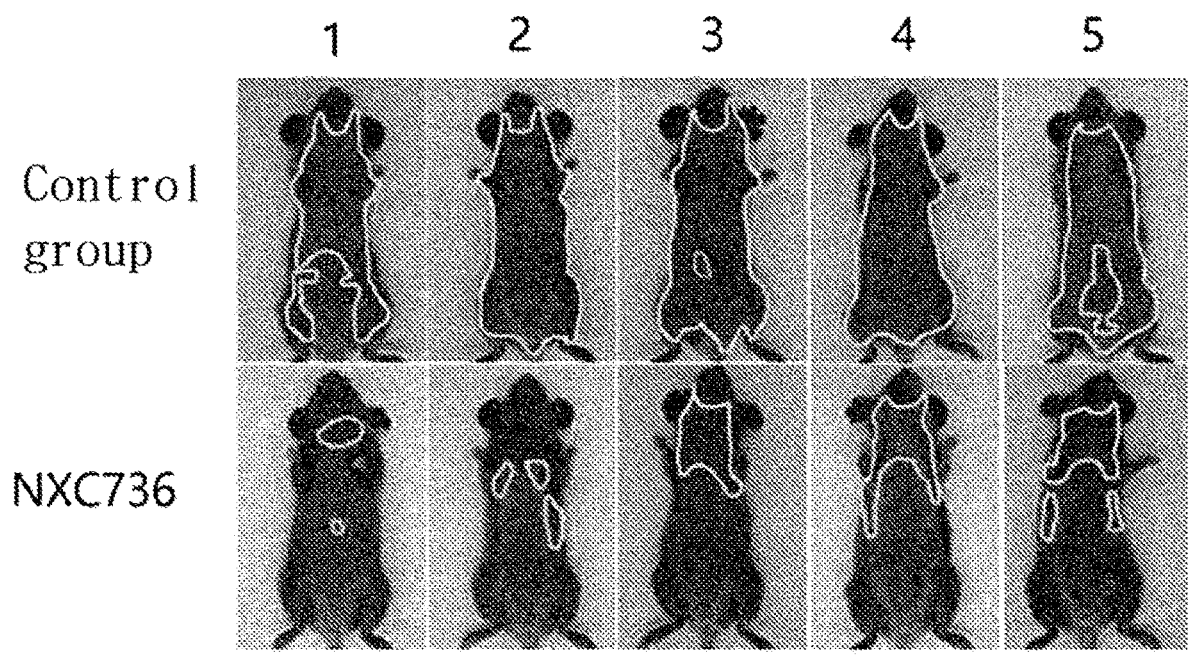
FIG. 5 shows the results of comparing the effect of suppressing alopecia areata induction according to oral administration of the control group and NXC736 (30 mg/kg/day) in the alopecia areata mouse model C3H/HeJ.

Meanwhile, referring to FIG. 5, at 84 days after drug administration, as a result of comparing the control group and the effect of suppressing alopecia areata induced by oral administration of NXC736, it was confirmed with the naked eye that the progression of alopecia areata was significantly delayed upon administration of NXC736.

For reference, no significant difference in body weight was identified between the control group and the NXC736 administration group.

Experimental Example 4: Evaluation of the Effect of NXC736 on the Cardiovascular System 1) Evaluation of the Effect of NXC736 on HEK293 Cells Overexpressing the hERG Gene NXC736 was applied to HEK-293 cells (Aurora Biomed Inc., Canada), which stably expressed the hERG potassium ion channel by introducing hERG (human Ether-à-go-go Related Gene), to evaluate its effect on hERG channel currents. NXC736 was set at concentrations of 1, 3, 10, and 30 μM.

On the day of the experiment, hERG channel currents were measured and cells measured above 500 pA and below 3000 pA at the −50 mV repolarization step were selected, and then test substances of each concentration dissolved in an external water bath solution (137 mM NaCl, 4 mM KCl, 10 mM HEPES, 1 mM $MgCl_2$, 10 mM D-glucose, 1.8 mM $CaCl_2$), pH 7.4) were treated for 9 minutes and the channel current was measured using the Notocord program (Notocord System, France).

As a negative control group, only an external water bath solution was used to record, and as a positive control group, a positive control substance (E-4031 n-Hydrate, FUJIFILM Wako Pure Chemical Corporation, Japan) was treated with 0.1 μM after washing for any one cell to confirm that hERG channel currents were suppressed through a record, thereby confirming the suitability of the cell line together.

Referring to FIG. 6, the compensated suppression rate (%) of hERG channel currents of NCX736 (B to E groups) at concentrations of 1, 3, 10, and 30 μM were 9.94±1.96, 13.98±4.48, 35.03±12.09, and 82.62±7.31% (n=3), respectively, and the compensated suppression rate (%) of hERG channel currents in the negative control group (A group) was 0±4.12 (n=3). That is, it was confirmed that NCX736 (D and E groups) at concentrations of 10 and 30 μM showed a statistically significant difference compared to the negative control group (A group).

In particular, as a result of treating the test substance NXC736 up to a concentration of 30 μM, the compensated suppression rate (%) of hERG channel currents was 82.62±7.31%, and $K^+$ ion channel inhibition ability (IC50) was calculated to be 12.94 μM (Hill coefficient: 1.527).

Meanwhile, in the results of treating E-4031 at a concentration of 0.1 μM as a positive control group (F group) under the same conditions, the compensated suppression rate (%) of hERG channel currents showed a high value of 92.64±1.66% (n=5).

Considering these results, it was confirmed that this test method is an appropriate method to evaluate the effect of NCX736 on hERG channel currents, and it was confirmed that NXC736 is a substance that does not inhibit hERG potassium channel activity and does not cause cardiac abnormalities.

2) Checking of the Effect on the Cardiovascular System Using Beagle Dogs

NXC736 was orally administered to four unanesthetized and unrestrained male beagle dogs (ORIENTBIO Inc., Republic of Korea) implanted with remote transmitters. Afterwards, the heart rate of four beagle dogs was measured to evaluate the effect of NXC736 on the cardiovascular system, and the occurrence of abnormal symptoms was visually checked.

In this experiment, 4 beagle dogs were administered with 0.5% MC aqueous solution, which is an excipient, as a control substance, and the heart rate was measured, and after 1 week, NXC736 was administered at 12.5 mg/kg and the heart rate was measured, after 1 week, NXC736 was administered at 25 mg/kg and the heart rate was measured, and after 1 week, NXC736 was administered at 50 mg/kg and the heart rate was measured.

The heart rate of beagle dogs was specifically measured at 0 hours before administration of the test substance, and 0.5 hours, 1 hour, 2 hours, 3 hours, 4 hours, 6 hours, 8 hours, 12 hours, and 24 hours after administration of the test substance.

Figure 7:
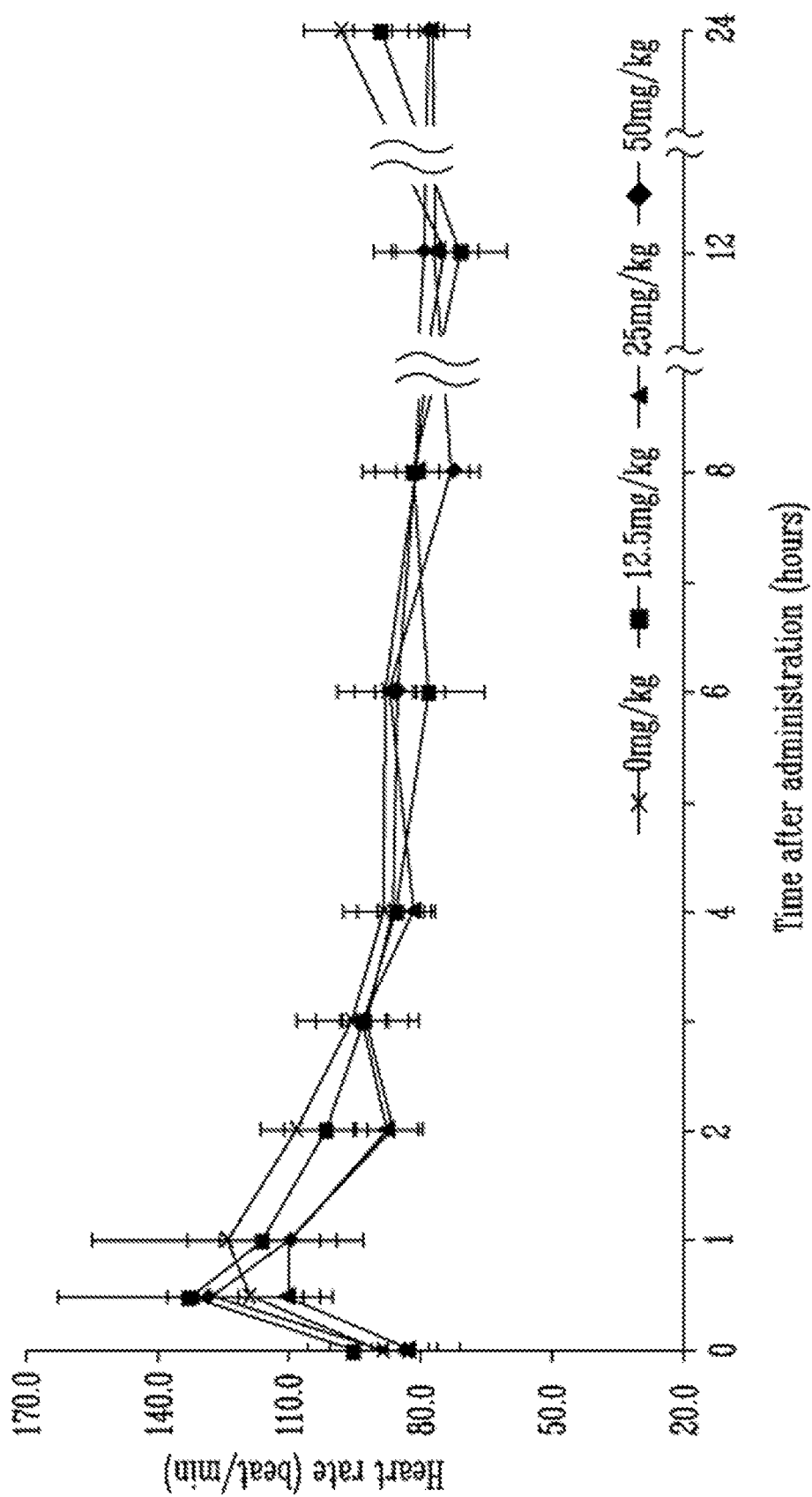
FIG. 7 is a graph showing the heart rate measurement results of beagle dogs after oral administration of NXC736 (12.5, 25, 50 mg/kg).

Referring to FIG. 7, it was confirmed that there was no change in heart rate even when NXC736 was administered at doses of 12.5, 25, and 50 mg/kg.

In addition, as a result of observing general symptoms of beagle dogs with the naked eye, no abnormal symptoms were observed when administering doses of 12.5, 25, or 50 mg/kg of NXC736.

As described above, according to the results of evaluating the efficacy of suppressing alopecia areata using the C3H/HeJ alopecia areata mouse model and the results of checking the heart rate of beagle dogs administered NXC736 and whether abnormal symptoms were observed with the naked eye, it was confirmed that the pharmaceutical composition containing the compound represented by Formula 1, an optical isomer thereof, or a pharmaceutically acceptable salt thereof according to the present invention as an active ingredient acts as a functional antagonist for S1PR1 and S1PR4 to prevent or treat alopecia areata. In addition, it was confirmed that the pharmaceutical composition according to the present invention acts as a functional antagonist for S1PR1 and S1PR4 among subtypes of S1P receptors (S1P1, S1P2, S1P3, S1P4 and S1P5), thereby having an effect of preventing or treating alopecia areata and also having an effect of not causing cardiovascular side effects.

What is claimed is:

1. A method for treating alopecia areata, comprising administering a compound represented by the following Formula 1, an optical isomer thereof, or a pharmaceutically acceptable salt thereof to a subject in need thereof:

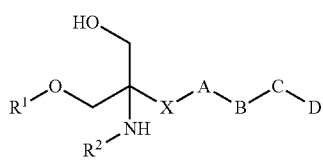

[Formula 1]

wherein,
$R^1$ is hydrogen;
$R^2$ is hydrogen or an acetyl group;
X is a single bond, $C_2$ alkylene, or $C_2$ alkenylene;
A is a 5-membered heteroarylene ring containing 3 N atoms;
B is $C_{2-11}$ straight- or branched-chain alkylene;
C is a single bond; and
D is selected from the group consisting of hydrogen, and $C_{1-6}$ alkyl.

2. The method of claim 1, wherein $R^2$ is hydrogen.
3. The method of claim 1, wherein X is $C_2$ alkylene.
4. The method of claim 1, wherein B is $C_{2-11}$ straight-chain alkylene.
5. The method of claim 1, wherein the compound represented by Formula 1 is any one compound selected from the group of compounds below:
   (1) 2-amino-2-(2-(1-decyl-1H-1,2,3-triazol-4-yl)ethyl)propane-1,3-diol;
   (2) 2-amino-2-(2-(1-octyl-1H-1,2,3-triazol-4-yl)ethyl)propane-1,3-diol;
   (4) 2-amino-2-(1-dodecyl-1H-1,2,3-triazol-4-yl)propane-1,3-diol;
   (5) (E)-2-amino-2-(1-decyl-1H-1,2,3-triazol-4-yl)vinyl-1,3-diol;

(7) N-(2-(1-dodecyl-1H-1,2,3-triazol-4-yl)-1,3-dihydroxypropan-2-yl)acetamide;
(8) N-(4-(1-decyl-1H-1,2,3-triazol-4-yl)-1-hydroxy-2-(hydroxymethyl)butan-2-yl)acetamide.

6. The method of claim 1, wherein the compound represented by Formula 1 is a compound represented by Formula 2 below:

[Formula 2]

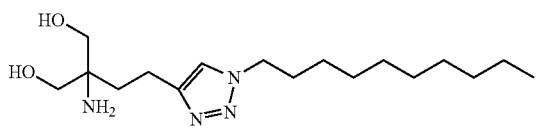 [SMILES: CCCCCCCCCCn1cc(CCC(N)(CO)CO)nn1]

7. The method of claim 1, wherein the compound represented by the following Formula 1, an optical isomer thereof, or a pharmaceutically acceptable salt thereof is administered orally or parenterally.

8. The method of claim 1, the compound, the optical isomer thereof or the pharmaceutically acceptable salt thereof is administered with one or more other therapeutic agents suitable for treating alopecia areata.

9. The method of claim 1, wherein the compound, the optical isomer thereof or the pharmaceutically acceptable salt thereof acts as a functional antagonist for S1PR1 and S1PR4.

10. The method of claim 9, wherein the compound, the optical isomer thereof or the pharmaceutically acceptable salt thereof does not cause cardiovascular side effects.

\* \* \* \* \*